(12) United States Patent
Wikström et al.

(10) Patent No.: US 6,998,405 B2
(45) Date of Patent: Feb. 14, 2006

(54) PHENYLETHYLAMINES AND CONDENSED RINGS VARIANTS AS PRODRUGS OF CATECHOLAMINES, AND THEIR USE

(75) Inventors: Håkan Wikström, Groningen (NL); Durk Dijkstra, Bedum (NL); Bastiaan Johan Venhuis, Groningen (NL)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 10/737,782

(22) Filed: Dec. 18, 2003

(65) Prior Publication Data

US 2004/0138281 A1  Jul. 15, 2004

Related U.S. Application Data

(62) Division of application No. 10/258,014, filed as application No. PCT/SE01/00840 on Apr. 17, 2001, now Pat. No. 6,683,087.

(30) Foreign Application Priority Data

Apr. 18, 2000 (SE) .................................... 0001438

(51) Int. Cl.
- *A61K 31/45* (2006.01)
- *C07D 221/06* (2006.01)
- *C07D 219/06* (2006.01)

(52) U.S. Cl. ................ 514/290; 514/297; 514/212.01; 514/411; 546/101; 548/427

(58) Field of Classification Search ................ 546/101; 548/427; 514/290, 297, 212.01, 411
See application file for complete search history.

(56) References Cited

U.S. PATENT DOCUMENTS

| 3,991,207 A | 11/1976 | Sarges et al. |
| 4,410,519 A | 10/1983 | Seiler et al. |
| 4,565,818 A | 1/1986 | Nordmann et al. |

FOREIGN PATENT DOCUMENTS

| DE | 5114325 | 11/1992 |
| EP | 0659430 | 6/1995 |
| WO | WO 91/00727 | 1/1991 |
| WO | WO 92/18475 | 10/1992 |
| WO | WO 00/06536 | 2/2000 |
| WO | WO 01/28977 | 4/2001 |

OTHER PUBLICATIONS

Tommy Litjefors et al., "Pre-and Postsynaptic Dopaminergic Activities of Indolizidine and Quinolizidine Derivatives of 3-(3-Hydroxyphenyl)-N-(n-propyl)piperidine (3-PPP) Further Developments of a Dopamine Receptor Model", J. Med Chem., vol. 33, 1990, pp. 1015-1022, Chart I.

(Continued)

Primary Examiner—Rita Desai
(74) Attorney, Agent, or Firm—McDermott Will & Emery LLP

(57) ABSTRACT

Compounds of the general formula I

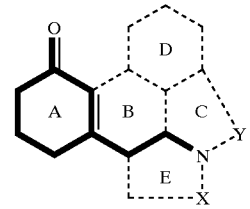

Formula I wherein rings B, C, D and E may be present or not and, when present, are combined with A as A+C, A+E, A+B+C, A+B+D, A+B+E, A+C+E, A+B+C+D or A+B+C+D+E, rings B, C and E being aliphatic whereas ring D may be aliphatic or aromatic/heteroaromatic, and wherein X is —$(CH_2)_m$—, in which m is an integer 1–3, to form a ring E or, when E is absent, a group $R_1$ bound to the nitrogen atom, wherein $R_1$ is selected from the group consisting of a hydrogen atom, alkyl or haloalkyl groups of 1 to 3 carbon atoms, cycloalkyl(alkyl) groups of 3 to 5 carbon atoms (i.e. including cyclopropyl, cyclopropylmethyl, cyclobutyl and cyclobutylmethyl) and wherein Y is —$(CH_2)_n$—, in which n is an integer 1–3, to form a ring C or when C is absent, a group $R_2$ bound to the nitrogen atom, wherein $R_2$ is selected from the group consisting of a hydrogen atom, alkyl or haloalkyl groups of 1 to 7 carbon atoms, cycloalkyl(alkyl) groups of 3 to 7 carbon atoms, alkenyl or alkylnyl groups of 3 to 6 carbon atoms, arylalkyl, heteroarylalkyl having 1 to 3 carbon atoms in the alkyl moiety, whilst the aryl/heteroaryl nucleus may be substituted, provided that when rings B, C, D and E are absent $NR_1R_2$ is different from dimethylamino, N-methyl-N-ethylamino, N-methyl-N-propynyl-amino, N-methyl-N-propylamino and N-hydroxipropyl-N-methylamino, and salts thereof with pharmaceutically acceptable acids or bases are disclosed as well as the use of such compounds for the manufacturing of pharmaceutical compositions for the treatment of Parkinson's disease, psychoses, Huntington's disease, impotence, renal failure, heart failure or hypertension, such pharmaceutical compositions and methods of treating Parkinson's disease and schizophrenia.

3 Claims, No Drawings

OTHER PUBLICATIONS

Klaus P. Bogeso et al., "Indolizidine and Quinolizidine Derivatives of the Dopamine Autoreceptor Agonist 3-(3-Hydroxyphenyl)-N-n-propylpideridine (3-PPP)", J. Med. Chem., vol. 30, 1987, pp. 142-150, Figure 1.

Cor J. Grol et al., "Resolution of 5,6-Dihydroxy-2-(N,N-di-n-propylamino)tetralin in Relation to the Structural and Stereochemical Requirements for Centrally Acting Dopamine Agonists", J. Med. Chem., vol. 28, 1985, pp. 679-683, scheme 1.

PHENYLETHYLAMINES AND CONDENSED RINGS VARIANTS AS PRODRUGS OF CATECHOLAMINES, AND THEIR USE

This application is a divisional of application Ser. No. 10/258,014 filed Oct. 18, 2002 now U.S. Pat. No. 6,683,087, which is a 371 of PCT/SE01/00840, filed Apr. 17, 2001.

FIELD OF THE INVENTION

The present invention relates to new chemical compounds representing a new prodrug principle for the generation of catecholamines, in particular catecholethylamines, to processes for their preparation, pharmaceutical compositions containing them and their use in therapy.

BACKGROUND ART

Neurodegenerative diseases are becoming more prevalent with the aging population. One particular neurodegenerative disease which typically has its onset between the ages of 50 and 80 years of age is Parkinson's disease. Parkinson's disease is a disorder of the brain which is characterized by tremor and difficulty with walking, movement, and coordination.

Parkinson's disease appears to be caused by a progressive deterioration of dopamine-containing neurons in the substantia nigra zona compacta of the brain. Dopamine is a chemical neurotransmitter which is utilized by brain cells to transmit impulses to control or modulate peripheral muscle movement. The loss of the dopamine-containing neurons results in reduced amounts of dopamine available to the body. Insufficient dopamine is thought to disturb the balance between dopamine and other neurotransmitters such as acetylcholine. When such dopamine levels are reduced, nerve cells cannot properly transmit impulses, resulting in a loss of muscle control and function.

Currently, there is no known cure for Parkinson's disease. Treatments are typically aimed at controlling the symptoms of Parkinson's disease, primarily by replacing the dopamine, with either L-DOPA which is metabolized to dopamine, or by administering chemical agents that stimulate dopamine receptors. Current treatments to slow the progression of the disease include compounds such as deprenyl (Selegeline), a selective monoamine oxidase inhibitor, and amantadine, a compound that appears to decrease dopamine uptake into presynaptic neurons.

Certain hydroxylated (mono-phenolic or catechols) phenylethylamines (as such or forming part of a semi-rigid/rigid ring system) are known to have useful dopaminergic activity. However, their clinical use is limited because they have low or no bioavailability (high first-pass effect).

It has been reported that (±)-5-keto-2-N,N-di-n-propylamino-tetrahydrotetralin ((±)-5-keto-DPATT (Formula A)) does possess dopaminergic effects in rats in vivo. However, in vitro binding of this compound does not take place, i.e. (±)-5-keto-DPATT has itself no affinity to DA receptors. Consequently, it must be bioactivated before displaying its effects. This was published on a poster by Steven Johnson at a local Med. Chem. Meeting in Ann Arbor, Mich., USA in 1994. There was no mentioning of catecholamine formation on that poster. However, it was speculated, but not shown, that the active drug may be (±)-5-OH-DPAT (see Formula B below). Consequently, the compound of Formula II, falling within the generally claimed structure of Formula I, is provisoed from the present invention.

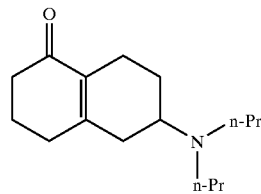

Formula A

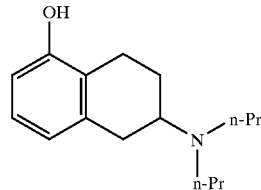

Formula B

In recent years a large body of pharmacological, biochemical and electrophysiological evidence has provided considerable support in favor of the existence of a specific population of central autoregulatory dopamine (DA receptors) located in the dopaminergic neuron itself and belonging to the D2 receptor subclass of DA receptors. These receptors are part of a homeostatic mechanism that modulates nerve impulse flow and transmitter synthesis and regulates the amount of DA released from the nerve endings. Recently, Sokoloff, et al., Nature, 347 146–51 (1990) presented evidence for the existence of a new type of dopamine receptor called D3. In a series of screened classical and a typical neuroleptics, the preferential dopamine autoreceptor antagonists (+)-AJ76 and (+)-UH232 possessed the highest preference for the D3 site. The D3 receptor appears to occur both pre- and postsynaptically, and the regional distribution (high preference in limbic brain areas) differs from that of the D1 and D2 receptors.

Drugs acting as agonists or antagonists on central DA transmission are clinically effective in treating a variety of central nervous system disorders such as parkinsonism, schizophrenia, Huntington's disease and other cognitive dysfunctions.

In parkinsonism, for example, the nigro-neostriatal hypofunction can be restored by an increase in postsynaptic DA receptor stimulation (see above)). In schizophrenia, the condition can be normalized by achieving a decrease in postsynaptic DA receptor stimulation. Classical antipsychotic agents directly block the postsynaptic DA receptor. The same effect can be achieved by inhibition of intraneuronal presynaptic events essential for the maintenance of adequate neurotransmission, transport mechanism and transmitter synthesis.

Direct DA receptor agonists, like apomorphine (a mixed DA D1/D2 agonist), are able to activate the DA autoreceptors as well as the postsynaptic DA receptors. The effects of autoreceptor stimulation appear to predominate when apomorphine is administered at low doses, whereas at higher doses the attenuation of DA transmission is outweighed by the enhancement of postsynaptic receptor stimulation. The antipsychotic and antidyskinetic effects in man of low doses of apomorphine are likely due to the autoreceptor-stimulator properties of this DA receptor agonist. This body of knowledge indicates DA receptor stimulants with a high selectivity for central nervous DA autoreceptors would be valuable in treating psychiatric disorders.

Compounds displaying preferential antagonistic effects at DA autoreceptors have been developed, Johansson et al., J. Med. Chem., 28, 1049 (1985). Examples of such compounds are (+)-cis-1S,2R-5-methoxy-1-methyl-2-(N-n-propylamino)tetralin ((+)-1S,2R-AJ76) and (+)-cis-1S,2R-5-methoxy-1-methyl-2-(N,N-di-n-propylamino)tetralin ((+)-1S,2R-UH232). Biochemically these compounds behave as classical DA antagonists, e.g. like haloperidol. Consequently, they raise the Dopa accumulation in normal animals after the blockage of aromatic amino acid decarboxylase by NSD1015 and they raise the levels of the DA metabolites DOPAC and HVA (no NSD1015 treatment). However, functionally, in behavioral testing (photocell motility meters), they display stimulatory properties, e.g. they increase the locomotor activity. In addition, gross behavioral observations show that these compounds, in certain dosages, can induce a weak classical dopaminergic stereotypic behavioral effects like sniffing and rearing in rodents.

Diseases in which an increase in dopaminergic turnover may be beneficial are geriatrics, for preventing bradykinesia and depression and in the improvement of mental functions (e.g. cognition). It can have an effect in depressed patients. It can be used in obesitas as an anorectic agent. It can improve minimal brain dysfunction (MBD), narcolepsy and negative symptoms of schizophrenia and, in addition, impotence, erectile dysfunction and restless legs. Thus, improvement of sexual functions is another indication (in both women and men).

DISCLOSURE OF THE INVENTION

It is an object of the present invention to provide new prodrugs which are uniquely metabolized in vivo to a catecholamine derivative that is a potent dopamine receptor ligand with agonist, partial agonist, inverse agonist and/or antagonist effects.

According to the present invention there is now provided new compounds having the general structural formula (I)

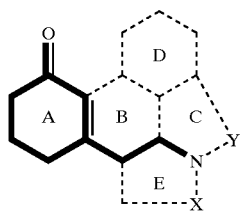

Formula I wherein rings B, C, D and E may be present or not and, when present, are combined with A as A+C, A+E, A+B+C, A+B+D, A+B+E, A+C+E, A+B+C+D or A+B+C+D+E, rings B, C and E being aliphatic whereas ring D may be aliphatic or aromatic/heteroaromatic, and wherein X is —$(CH_2)_m$—, in which m is an integer 1–3, to form a ring E or, when E is absent, a group $R_1$ bound to the nitrogen atom, wherein $R_1$ is selected from the group consisting of a hydrogen atom, alkyl or haloalkyl groups of 1 to 3 carbon atoms, cycloalkyl(alkyl) groups of 3 to 5 carbon atoms (i.e. including cyclopropyl, cyclopropylmethyl, cyclobutyl and cyclobutylmethyl) and wherein Y is —$(CH_2)_n$—, in which n is an integer 1–3, to form a ring C or when C is absent, a group $R_2$ bound to the nitrogen atom, wherein $R_2$ is selected from the group consisting of a hydrogen atom, alkyl or haloalkyl groups of 1 to 7 carbon atoms, cycloalkyl(alkyl) groups of 3 to 7 carbon atoms, alkenyl or alkylnyl groups of 3 to 6 carbon atoms, arylalkyl, heteroarylalkyl having 1 to 3 carbon atoms in the alkyl moiety, whilst the aryl/heteroaryl nucleus may be substituted, provided that when rings B, C, D and E are absent $NR_1R_2$ is different from dimethylamino, N-methyl-N-ethylamino, N-methyl-N-propynyl-amino, N-methyl-N-propylamino and N-hydroxipropyl-N-methylamino, and salts thereof with pharmaceutically acceptable acids or bases.

The compounds thus disclaimed are known per se but their therapeutical use has not been disclosed previously.

Thus the present invention provides the following classes of compounds based on the different combinations of rings A to E:

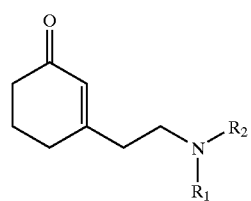

Formula Ia

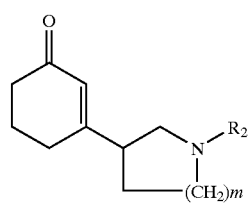

Formula Ib

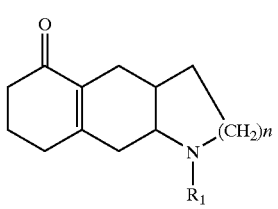

Formula Ie

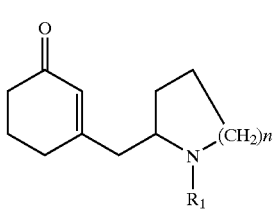

Formula Ic

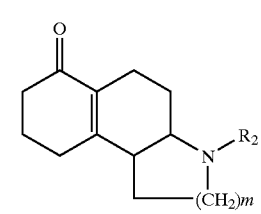

Formula If

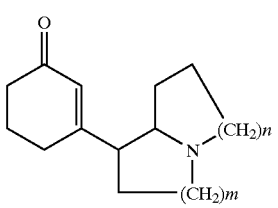

Formula Id

-continued

Formula Ig

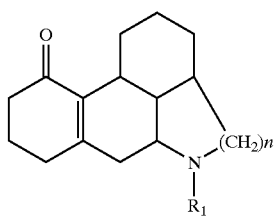

Formula Ih

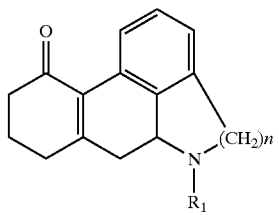

Formula Ii

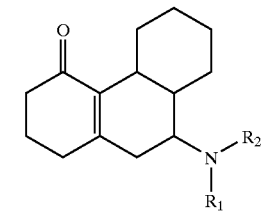

Formula Ik

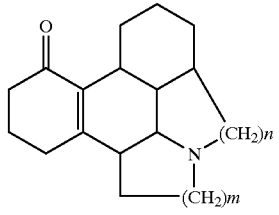

wherein $R_1$, $R_2$, m and n are defined as above.

The preferred combinations for rings A to E are A+B+C (formula Ie), A+B+C+D (formula Ig), A+B+E (formula If), A+E (formula Ib) and A+C+E (formula Id), the most preferred combination being that of A+B+C (formula Ie).

The preferred meaning of $R_1$ and $R_2$ is n-propyl.

It will be apparent to those skilled in the art that compounds of this invention contain one or several chiral centers. The compounds of Formula I contain asymmetric carbon atoms in the alphatic ring moieties. The scope of this invention includes all (theoretically possible) R/S-combinations of the compounds of Formula I in their pure form. In general, the flatter a molecule of Formula I is the more potent it is as a dopaminergic agonist, provided it has a suitable n-alkyl substituent. Flat molecules of Formula I are those which have transfused ring systems.

Since the pharmaceutical activity of the racemates or the different combinations of R/S at the chiral C atoms in a molecule of the present invention can differ, it may be desirable to use as "chirally" pure forms as possible (e.g. the examples given below). In these cases, the final product or else even the intermediates can be resolved into enantiomeric compounds by chemical or physical measures known to the person skilled in the art or even employed in the synthesis as such.

Preferred absolute configurrations of compounds of Formula Ia–h

Formula Ib

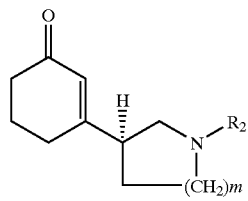

Formula Id

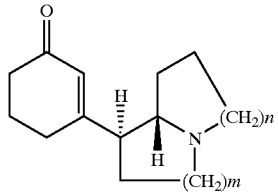

Formula Ie

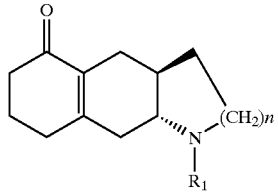

Formula If

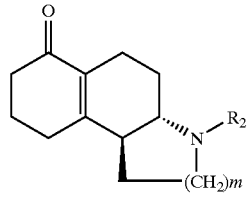

Formula Ig

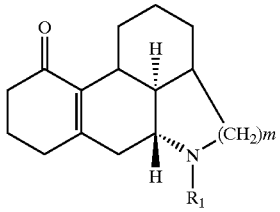

Formula Ih

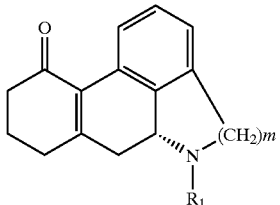

wherein $R_1$, $R_2$, m and n are defined as above.

The prodrugs according to the present invention display useful therepeutic effects for the treatment of diseases like (in the central nervous systen (CNS)): Parkinson's disease, psychoses (e.g. schizophrenia), Huntington's disease, impotence; (in the periphery): renal failure, heart failure and hypertension. Other fields of therapeutically active catecholamines are adrenergic, anti-adrenergic compounds.

Some of the compounds according to the invention have both pre- and postsynaptic antagonistic effects. Compounds possessing more of the postsynaptic effects can be used to alleviate the symptoms (both positive and negative) of schizophrenia and for the rehabilitation of drug addicts. Other disturbances of interest in this context is "jet lag", sleep disorders and early stages of Parkinsonism. Another indication for the compounds of this invention are diseases with a disturbed cognition, e.g. Huntington's disease and Alzheimer's disease.

Other diseases/conditions, beside Parkinson's disease, which can be treated with the compounds, in a suitable formulation, of the present invention are restless legs syndrome (RLS), erectile dysfunction (impotence in men) and sexual stimulation in e.g. menopausal women (stimulation of vaginal lubrication and erection of clitoris). In the autoreceptor dose-range, corresponding to a low plasma and striatal tissue concentration of compounds of the present invention can also be used to treat psychoses (e.g. schizophrenia; see above).

The herewith mentioned diseases do not form a limitation to the present invention, thus, other diseased states involving the DA-ergic system may also be relevant for treatment with compounds of the present invention.

The compounds of Formula I may be converted to their respective "built-in" 3,4-di-OH-phenylethylamines, (Formula II), in vivo in the CNS and/or the periphery.

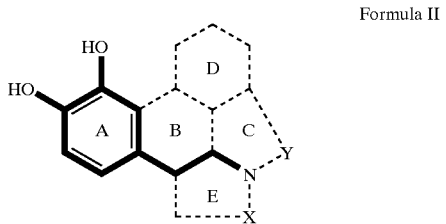

Formula II wherein X, Y, $R_1$, $R_2$, m and n are defined as above in connection with formula I.

It is possible that the compounds of Formula II appear in the brain cells of animals following oral and parenteral administration of the compounds of Formula I. Therefore, in accordance with the present invention, applicants have surprisingly found that cyclohexenone-ethylamines of the general structure of Formula I above are bio-activated in vivo, likely to the corresponding 3,4-di-OH-phenylethylamines (Formula II).

Compounds of formula II may also possess properties of catechol-O-methyl-transferase (COMT) inhibition, an effect which may synergistically augment the dopaminergic effects of the catechols generated.

The compounds of the present invention can be administered to a patient either alone or as a part of a pharmaceutical composition.

The term "patient" as used herein means all animals including humans. Examples of patients include humans, rodents, and monkeys.

Thus, according to another aspect of the present invention here is provided a pharmaceutical composition which as the active principle contains a compound of formula I as defined above, however with no disclaimer in the meaning of $NR_1R_2$ when rings B, C, D and E are absent, or a pharmaceutically acceptable salt thereof together with a pharmaceutically acceptable carrier, diluent, or excipient.

The pharmaceutical compositions of the present invention can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

A preferred route of administration is oral, although parenteral and transdermal administration are also contemplated. Controlled release formulations particularly in the form of skin patches and the like, are particularly well-suited treating elderly patients.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents solvents or vehicles include water, ethanol, polyols (propylene glycol, polyethylene glycol, glycerol, and the like), suitable mixtures thereof, vegetable (such as olive oil, sesame oil and viscoleo) and injectable organic esters such as ethyl oleate. Proper fluidity can be maintained, for example, by the use of a coating such as lecithin, by the maintenance of the required particle size in the case of dispersions and by the surfactants.

These compositions may also contain adjuvants such as preserving, emulsifying, and dispensing agents. Prevention of the action of microorganisms be controlled by addition of any of various antibacterial and antifungal agents, example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Oral delivery of the invention compounds is preferred, given the typical age of the patient population and the condition being treated. Solid dosage forms for oral administration include capsules, tablets, pills, powders and granules. In such solid dosage forms, the active compound is admixed with at least one inert customary excipient (or carrier) such as sodium citrate or dicalcium phosphate or:
(a) fillers or extenders, as for example, starches, lactose, sucrose, glucose, mannitol and silicic acid,
(b) binders, as for example, carboxymethylcellulose, alginates, gelatin, polyvinylpyrrolidone, sucrose, and acacia,
(c) humectants, as for example, glycerol
(d) disintegrating agents, as for example, agar-agar, calcium carbonate, potato or tapioca starch, alginic acid, certain complex silicates, and sodium carbonate,
(e) solution retarders, as for example paraffin,
(f) absorption accelerators, as for example, quaternary ammonium compounds,
(g) wetting agents, as for example cetyl alcohol, and glycerol monostearate,
(h) adsorbents, as for example, kaolin and bentonite, and
(i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar and as high molecular weight polyethylene glycols, and the like.

Solid dosage forms such as tablets, dragées, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be used in micro-encapsulated form, if appropriate, with one or more of the above-mentioned excipients. Controlled slow release formulations are also preferred, including osmotic pumps and layered delivery systems.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, viscoleo, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated iso-stearyl alcohols, polyoxyethylene sorbitol and sorbitan esters, microcrystalline cellulose, aluminum metahydroxide, bentonite agar-agar and tragacanth, or mixtures of these substances, and the like.

Compositions for rectal administrations are preferably suppositories which can be prepared by mixing the compounds of the present invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts" as used herein refers to those amino acid addition salts of the compound of the present invention which are, the scope of sound medical judgment, suitable for use in contact with the tissues of patients without undue toxicity, irritation, allergic response, and the like, commensurate with a reasonable benefit/risk ratio, and effective for their intended use as well as the zwitterionic forms, where possible, of the compounds of the invention. The term "salts" refers to the relatively non-toxic, inorganic and organic acid addition salts of the compounds of Formula I. These salts can be prepared in situ during the final isolation and purification of the compounds of the invention or by separately reacting the purified compound in the free base form with a suitable organic or inorganic acid and isolating the salt thus formed. Representative salts include the hydrobromide, hydrochloride, sulfate, bisulfate, nitrate, acetate, ox-alate, valerate, oleate, palmitate, sstarate, laurate, borate, benzoate, lactate, phosphate, tosylate, citrate, maleate, fumarate, succinate, tartrate, naphthylate, mesylate, glucoheptonate, lactobionate and laurylsulphonate salts, and the like. These may include cations based on the alkali and alkaline earth metals, such as sodium, potassium, calcium, magnesium, and the like, as well as nontoxic ammonium, quatemary ammonium and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," J. Pharm. Sci., 1977; 66:1–19 which is incorporated herein by reference.) In addition, the compounds of the present invention can exist in unsolvated as well as solvated form with pharmaceutically accepted solvents such as water, ethanol, and the like. In general, the solvated forms are considered equivalent to the unsolvated forms for the purposes of the present invention.

According to a further aspect of the present invention there is provided a method of treating Parkinson's disease in a patient in need thereof, which method comprises administering to the patient a therapeutically effective amount of a compound of any of formulae Ie, If and Ig, defined as above, or a pharmaceutically acceptable salt thereof.

A "therapeutically effective amount" is an amount of a compound of Formula I, that when administered to a patient, ameliorates a symptom of Parkinson's disease.

Those skilled in the art are easily able to identify patients having Parkinson's disease. For example, patients who exhibit symptoms which include, but are not limited to, tremor and/or shaking and difficulty with walking, other movement, and coordination.

According to another aspect of the present invention there is provided a method of treating schizophrenia in a patient in need thereof, which method comprises administering to the patient a therapeutically effective amount of a compound of any of formulae Ib and Id, defined as above, or a pharmaceutically acceptable salt thereof.

The compounds of the present invention can be administered to a patient at dosage levels in the range of about 0.01 to about 1,000 mg per day. For a human adult having a body weight of about 70 kilograms, a dosage in the range of about 0.001 to about 100 mg per kilogram of body weight per day is preferable. The specific dosage used, however, can vary. For example, the dosage can depend on a number of factors including the requirements of the patient, the severity of the condition being treated, and the pharmacological activity of the compound being used. The determination of optimum dosages for a particular patient is well-known to those skilled in the art.

In addition, it is intended that the present invention cover compounds made either using standard organic synthetic techniques, including combinatorial chemistry or by biological methods, such as through metabolism. The examples presented below are intended to illustrate particular embodiments of the invention and are not intended to limit the scope of the specification, including the claims, in any way.

The compounds of Formula I, utilized in the method of the present invention, are ideally suited for several reasons. Firstly, the compounds are stable, making them excellent candidates for oral administration. Secondly, the compounds are long acting, thereby enabling effective treatment with fewer dosing intervals, which is of significant importance for elderly patients. Thirdly, the compounds of the present invention have excellent oral bioavailabilities.

According to a further aspect the present invention provides the compounds of formula (I) as defined above, however with no disclaimer in the meaning of $NR_1R_2$ when rings B, C, D and E are absent, and the pharmaceutically acceptable salts thereof, for therapeutical use.

According to yet another aspect the present invention comprises the use of the compounds of formula (I) as defined above, however with no disclaimer in the meaning of $NR_1R_2$ when rings B, C, D and E are absent, and the pharmaceutically acceptable salts thereof for the manufacturing of pharmaceutical compositions for the treatment of Parkinson's disease, psychoses, Huntington's disease, impotence, renal failure, heart failure or hypertension.

The following detailed examples illustrate the general synthetic techniques utilized for preparing the compounds, along with some of the biological assays employed to establish the efficacy of the compounds of the present invention.

EXAMPLES (Alkylated) Dopamine Prodrugs

Scheme 1) Prodrugs of (Alkylated) Dopamine:

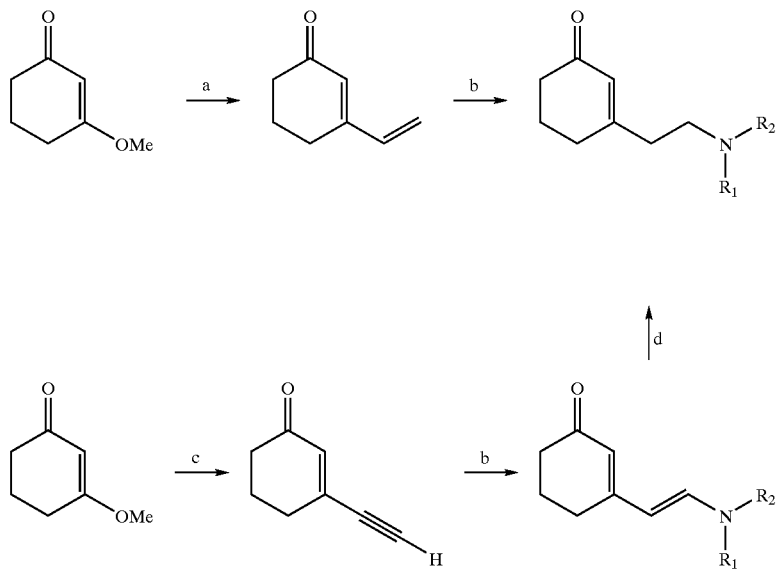

Reagents: (a) $CH_2$═$CHMgBr$; (b) $R1R2NH$, $Cs2CO3$
(c) $CH$≡$CMgBr$; (d) $NaBH3CN$

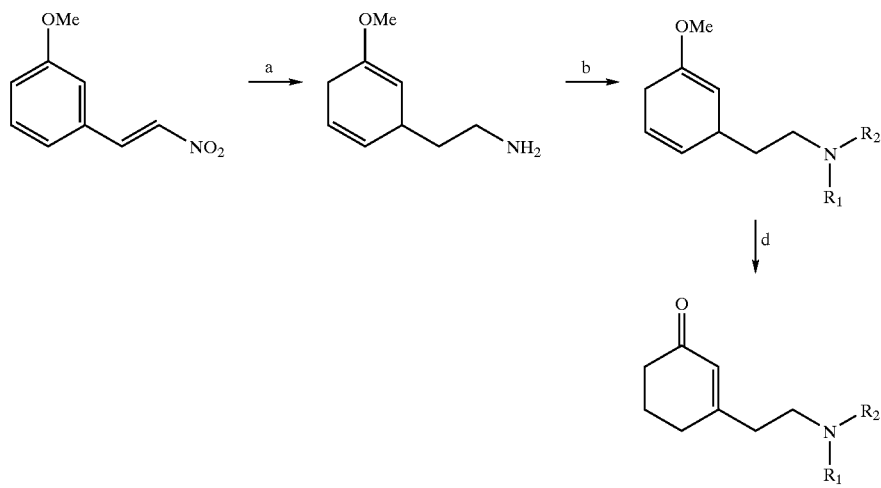

Reagent: (a) i) $Li/NH3$, $tBuOH$, 2 h, ii) MeOH
(b) Alkylating or acylating agent
(c) $H+/H2O$.

The lower scheme represents a Birch reduction.

Example 1

3-(2-Dipropylamino-ethyl)-cyclohex-2-enone (GMC6598)

3-Vinyl-cyclohex-2-enone (0.75 g, 6.1 mmol) (prepared according to Nasarow's method) was dissolved in acetonitril (1 mL) and dipropylamine (1.5 g, 16 mmol) was added followed by $Cs_2CO_3$ (50 mg). After stirring the mixture at rt for 3 h it was diluted with diethylether (100 mL), filtered and evaporated to dryness. The residue was destined in vacuo (175° C., 0.01 mm Hg) to give a slightly yellow oil which was converted to the hydrochloride salt. Recrystallization from isopropyl ether/isopropyl alcohol yielded: 1.2 g, 4.6 mmol (75%), mp 95–97° C. IR (KBr) 2962, 2613, 1667; $^1$H-NMR (CDCl$_3$) δ 5.84 (d, 1H), 2.65 (m, 2H), 2.27–2.60 (m, 9H), 1.99 (m, 2H), 1.39–1.51 (m, 5H), 0.86 (t, 6H) ppm; $^{13}$C-NMR (CDCl$_3$) δ 198.2, 163.5, 124.9, 54.2, 50.1, 35.7, 33.7, 28.4, 21.2, 18.5, 10.4 ppm; MS (EI) m/z 223 (M$^+$).

Example 2

3-(2-Diethylamino-ethyl)-cyclohex-2-enone (GMC6608)

The same procedure was used as in Example 1 but using diethylamine. Destillation at 120° C., 0.01 mmHg afforded a colorless oil that was converted to the hydrochloride salt. Recrystallization from isopropyl ether/isopropyl alcohol yielded: 1.3 g, 5.6 mmol (91%), mp 148–149° C. IR (KBr) 2948, 2851, 1661; $^1$H-NMR (CDCl$_3$) δ 5.86 (d, 1H), 2.48–2.67 (m, 6H), 2.27–2.39 (m, 6H), 1.96 (m, 2H), 1.02 (t, 6H) ppm; $^{13}$C-NMR (CDCl$_3$) δ 198.3, 163.5, 124.8, 48.9, 45.2, 35.7, 33.7, 28.4, 21.2, 10.1 ppm; MS (EI) m/z 195 (M$^+$).

Example 3

3-(2-Dibutylamino-ethyl)-cyclohex-2-enone (GMC6623)

The same procedure was used as in Example 1 but using dibutylamine. Purification by column chromatography (silica, ethyl acetate) yielded a colorless oil that was converted to the hydrochloride salt. Recrystallisation from isopropyl ether/isopropyl alcohol gave 1.3 g, 5.6 mmol (91%), mp 115–117° C. IR (KBr) 2959, 2494, 1661; $^1$H-NMR (CDCl$_3$) δ 5.84 (d, 1H), 2.60 (q, 2H), 2.26–2.44 (m, 8H), 1.96 (m, 3H), 1.21–1.46 (m, 8H), 0.87 (t, 6H) ppm; $^{13}$C-NMR (CDCl$_3$) δ 198.2, 163.6, 124.9, 52.0, 50.2, 35.7, 33.8, 28.4, 27.5, 21.2, 19.1, 12.5 ppm; MS (CI) m/z 252 (M+1).

Example 4

3-(2-((2-Phenyl)ethyl-propylamino)-ethyl)-cyclohex-2-enone (GMC6624)

The same procedure was used as in Example 1 but using N-propyl-2-phenylethylamine. Purification by column chromatography (silica, ethyl acetate) yielded a colorless oil that was converted to the hydrochloride salt. Recrystallisation from ether/ethanol gave 1.8 g, 5.6 mmol (91%), mp 110–112° C. IR (KBr) 2937, 2538, 2442, 1667; $^1$H-NMR (CDCl$_3$) δ 7.15–7.83 (m, 5H), 5.95 (s, 1H), 3.07 (t, 2H), 2.83, (q, 2H), 2.27–2.50 (m, 6H), 2.04 (p, 4H), 1.47–1.64 (m, 4H), 0.86 (t, 3H) ppm; $^{13}$C-NMR (CDCl$_3$) δ 198.2, 163.5, 136.4, 127.2, 127.0, 126.7, 119.2, 48.1, 42.7, 42.4, 36.2, 34.0, 32.2, 22.8, 20.7, 20.3, 9.4 ppm; MS (CI) m/z 286 (M+1).

N-n-Propyl-3-(3,4-di-hydroxyphenyl)piperidine PRO-DRUG Scheme 2) Prodrug of 3-APC (Alkylpyridinecatechol)

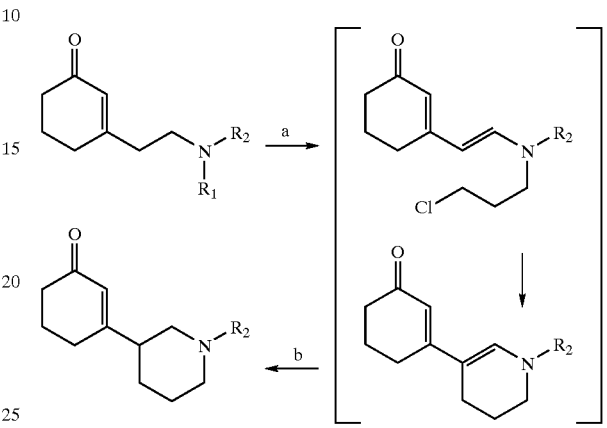

Reagents: (a) Chloropropyl-alkylamine; (b) NaBH3CN

As for the dopamine prodrug, the same possibility for a Birch reduction is present

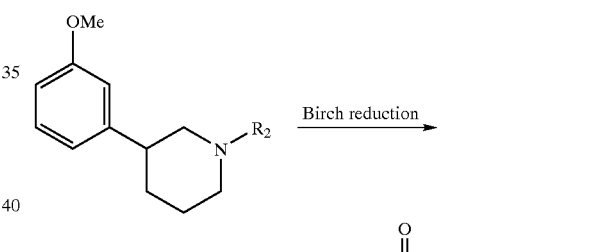

Example 5 a) 3-Ethynyl-2-cyclohexen-1-one (GMC6573)

To a solution of 0.5N ethynylmagnesium bromide in tetrahydrofuran (100 mL) was added under N$_2$ and stirring 3-ethoxy-2-cyclohexen-1-one (3.75 g, 26.8 mmol) in tetrahydrofuran (12.5 mL). The mixture was stirred at RT for 20 h when it was acidified with 1N HCl (200 mL). After stirring for 15 min the acidic phase was extracted with dichloromethane (5×50 mL). The combined organic extracts were washed with water (2×50 mL) and dried (MgSO$_4$). Evaporation of the solvent gave an oil that was purified by column chromatography (silica, ethyl acetate/hexane 1:9) to yield a yellow oil, 2.71 g, 22.6 mmol, 84%). Analysis were in agreement with literature data.

b) 3-(1-Propyl-1,4,5,6-tetrahydro-pyridin-3-yl)-cyclohex-2-enone (GMC6602)

3-Ethynyl-cyclohex-2-enone (3.20 g, 26.8 mmol) (from a) above) and (3-Chloro-propyl)-propyl-amine (4.50 g, 33.2 mmol) were mixed in acetonitril (50 mL). Cs$_2$CO$_3$ (100 mg) and KI (200 mg) were added and the mixture was refluxed under N$_2$ for 10 h. After cooling the mixture was diluted with water (50 mL) and extracted with dichloromethane (3×50 mL). The combined organic layers were washed with brine, dried (MgSO$_4$) and evaporated. The resulting dark oil was purified by column chromatography (silica, ethyl acetate) to give a yellow red oil. Yield 5.1 g, 23.3 mmol (87%). IR (neat) 2932, 2871, 1589, 1538, 1157 cm$^{-1}$; $^1$H-NMR (CDCl$_3$) δ 6.84 (s, 1H), 5.69 (s, 1H), 3.04–3.12 (m, 4H), 2.44 (t, 2H), 2.33 (t, 2H), 2.18 (t, 2H), 1.83–2.03 (m, 4H), 1.49–1.64 (m, 2H), 0.87 (t, 3H) ppm; $^{13}$C-NMR (CDCl$_3$) δ 197.0, 158.5, 140.1, 112.1, 102.4, 56.6, 44.3, 35.6, 23.6, 21.4, 20.2, 20.1, 19.7, 9.6 ppm; MS (CI) m/z 220 (M+1).

c) 3-(1-Propyl-piperidin-3-yl)-cyclohex-2-enone (GMC6606)

3-(1-Propyl-1,4,5,6-tetrahydro-pyridin-3-yl)-cyclohex-2-enone (5.0 g, 22.8 mmol) (from b) above) was dissolved in THF (100 mL). At 0° C., acetic acid (1.38 mL, 22.8 mmol) was added followed by introduction of NaBH$_3$CN (1.9 g, 30.0 mmol) in small portions maintaining the temperature. After the addition was complete the mixture was stirred for 1 h at this temperature and then at rt overnight. Work-up by addition of water (50 mL) and saturated aqueous NaHCO$_3$ (50 mL) followed by extraction with dichloromethane (5×50 mL). The combined organic layers were dried (MgSO$_4$) and evaporated. The residue was purified by column chromatography (silica, dichloromethane/ethanol 20:1) to give a colorless oil which was converted to the hydrochloride. Recrystallisation from isoprylether gave 4.2 g, 17.5 mmol (77%), mp 184–185° C. IR (KBr) 3396, 2941, 2469, 1667, 1455 cm$^{-1}$; $^1$H-NMR (CDCl$_3$) δ 5.83 (s, 1H), 3.85 (d, 2H), 2.29–2.56 (m, 7H), 1.23–2.17 (m, 10H), 0.88 (t, 3H) ppm; $^{13}$C-NMR (CDCl$_3$) δ 198.4, 165.1, 123.4, 59.0, 55.6, 51.9, 41.6, 36.0, 27.3, 26.9, 22.8, 21.2, 17.6, 10.2 ppm; MS (EI) m/z 221 (M+).

Benzo[g]quinoline Prodrug

Scheme 3) Prodrug of benzo [g] quinolines:

Reagents: (a) H$_2$, Pd/C; (b) SOCl$_2$, RNH2; (c) LiAlH$_4$; (d) Li, NH$_3$; (e) EtO$_2$C(CH$_2$)$_3$P(Ph)$_3$Br, K$^t$OBu; (f) PPA.

Or a different strategy:

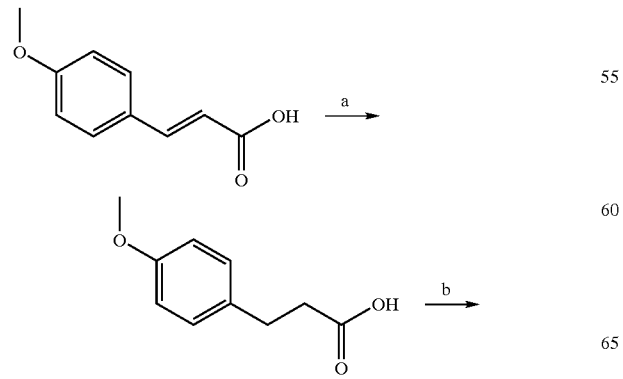

-continued

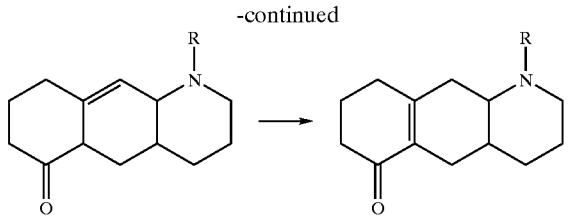

Example 6 a) 3-(4-methoxyphenyl)-propionic acid n-propylamide (GMC6632)

3-(4-methoxyphenyl)-propionic acid (8.8 g, 49 mmol) was refluxed in dichloromethane (200 mL) with thionylchloride (6.6 mL, 90 mmol) for 1 h. The volatiles were evaporated and the resulting oil was dissolved in dichloromethane (100 mL). This was added to a vigorously stirred mixture of 5% aqueous NaOH (200 mL), dichloromethane (100 mL) and n-propylamine (3.0 mL, 71 mmol). After stirring for 1 h the layers were separated and the aqueous layer was extracted with dichloromethane (3×50 mL). The combined organic layers were washed with water (50 mL) and brine (50 mL) and was dried over MgSO$_4$. Evaporation of the solvent gave the amide in quantitative yield (10.7 g, 49 mmol, 100%). IR (neat) cm$^{-1}$ 3300, 2961; 1734, 1642; MS (EI) m/z 221 (M+) Analyses were in agreement with literature data.

b) N-(3-(4-methoxyphenyl)-propyl)-N-propylamine (GMC6633)

To a stirred mixture of LiAlH$_4$ (8.0 g, 200 mmol) in tetrahydrofuran (100 mL) was added dropwise a solution of 3-(4-methoxyphenyl)-propionic acid n-propyl amid (10.7 g, 49 mmol) (from a) above) in tetrahydrofuran (100 mL). After refluxing for 12 h the mixture was cooled to 50° C. and excess hydride was destroyed by careful addition of water (10 mL), 5% aqueous NaOH (40 mL) and water (20 mL) allowing reflux conditions. The hot slurry was filtered and the white precipitate was washed thoroughly with ethanol. Volatiles were evaporated and the resulting oil dissolved in ethyl acetate (50 mL) what was extracted with 0.5 N aqueous HCl (4×50 mL). The acidic phase was made alkaline (pH=9) by addition of 30% aqueous NaOH and extracted with ethyl acetate (4×50 mL). The organic layers were combined, washed with brine, dried (MgSO$_4$) and evaporated to dryness to give an oil that partially crystallized in diethyl ether as the hydrochloride salt. Recrystallization from acetone/diethyl ether gave white flacky crystalline material. Total yield (as free base): 9.9 g, 48 mmol, 98%, mp 176–177° C. IR (neat) cm$^{-1}$ 2960, 2772, 1611, 1514; $^1$H-NMR (CDCl$_3$) δ 9.46 (br s, 1H), 7.16 (d, 2H), 6.90 (d, 2H), 3.72 (s, 3H), 2.82 (br s, 4H), 2.59 (t, 2H), 2.15 (p, 2H), 1.83 (h, 2H), 0.89 (t, 3H) ppm; $^{13}$C-NMR (CDCl$_3$) δ 156.6, 130.3, 127.7, 112.4, 53.7, 47.9, 45.66, 30.3, 25.9, 17.8, 9.7 ppm; MS (EI) m/z 207 (M+).

c) trans-N-propyl-7-keto-1,2,3,4,4a,5,8,8a-octahydro-[6H]-quinoline (GMC6638)

N-(3-(4-methoxyphenyl)-propyl)-N-propyl amine (6.15 g, 31.45 mmol) (from b) above) was dissolved in THF (60 mL), t-BuOH (4.65 g, 5.93 mL, 62.89 mmol). The mixture was cooled to −60° C. and liquid NH$_3$ (60 mL) was introduced. Then Li metal (1.70 g, 0.24 mol) was gradually added in small portions and the blue mixture was stirred at −60° C. for 4 h. The color was discharged by addition of a MeOH/aqueous NH$_4$Cl (sat) solution (1:1, 20 mL) and the cooling bath removed. After NH$_3$ had evaporated the pH of the slurry was adjusted to 1 by addition of concentrated hydrochloric acid and stirred for 24 h. Then the mixture was basified to pH 10 (30% NaOH, T<15° C.) and solid NaCl was introduced until the organic layer separated. The aqueous solution was extracted with dichloromethane (8×50 mL) and the combined organic layers ware washed with brine and dried over MgSO$_4$. Evaporation yielded a red oil that was purified by column chromatography (silica, dichloromethane/ethanol, 20:1) to yield a colorless oil (4.69 g, 24.05 mmol, 76%). A sample was converted to the hydrochloride for analysis, mp 148–150° C. IR (KBr) 2950, 2384, 1711, 1464 cm$^{-1}$; $^1$H-NMR (CDCl$_3$) δ 3.10 (dt, 1H, J=3.91 Hz, 9.52 Hz), 1.23–1.80 (m, 7H), 1.93–2.72 (m, 10H), 0.84 (t, 3H) ppm; $^{13}$C-NMR (CDCl$_3$) δ 210.4, 59.5, 54.3, 46.3, 36.6, 36.0, 33.7, 26.8, 23.6, 22.7, 18.0, 10.3 ppm; MS (EI) m/z 195 (M+).

d) L-Propyl-trans-2,3,4,4a,5,7,8,9,10,10a-decahydrobenzo[g]quinolin-6-one (GMC6650) and 1-Propyl-cis-2,3,4,4a,5,7,8,9,10,10a-decahydrobenzo[g]quinolin-6-one (GMC6651)

To a cooled (0° C.) suspension of KO$^t$Bu (2.5 g, 25.6 mmol) in dry dimethylformamide (4 mL) flushed with N$_2$ was added dropwise a solution of (3-ethoxycarbonylpropyl)triphenylphosphonium bromide (12.9 g, 28.2 mmol) in dry, N$_2$ flushed dimethylformamide (25 mL). When the addition was complete the mixture was stirred at 0° C. for 30 min. Then a solution of trans-N-propyl-7-keto-1,2,3,4,4a,5,8,8a-octahydro-[6H]-quinoline (2.5 g, 12.8 mmol) (from c) above) in dry, N$_2$ flushed dimethylformamide (4 mL) was added dropwise at 0° C. After stirring at 0° C. for 4 h the temperature was allowed to rise to RT and stirring was continued overnight. Water (50 mL) was added and the mixture was filtered through Celite (2 g). The filtrate was extracted with hexane (5×25 mL). The combined organic layers were dried (MgSO$_4$), filtered and evaporated to give a beige solid (9.1 g). The solid was dissolved in dichloromethane (10 mL) and was added to PPA (40 g) at 100° C. while stirring. After 4 h stirring at that temperature the reaction mixture was allowed to cool to about 80° C. when crushed ice (50 g) was introduced. Stirring was continued at that temeprature for 1 h and then the solution was allowed to cool to RT. Concentrated ammonia was added until pH=8 and then the solution was extracted with dichloromethane (6×100 mL). The combined organic layers were dried (MgSO$_4$), filtered and evaporated. The residue was purified by column chromatography (silica, dichloromethane/methanol, gradient) and the products were subsequently converted to the hydrochloric salt and recrystallized from diethyl ether/ethanol.

Cis isomer: Yield 0.07 g, 0.3 mmol (6%). IR (KBr) 2928, 2592, 1668, 1457, 1394 cm$^{-1}$; $^1$H-NMR 500 MHz (CDCl$_3$) δ 3.20 (t, 1H, J=11 Hz), 2.75 (d, 1H), 2.00–2.58 (m, 12H) 1.82–2.00 (m, 2H), 1.52–1.79 (m, 4H), 1.38 (d, 1H), 1.22–1.29 (dq, 1H), 0.90 (t, 3H) ppm; $^{13}$C-NMR (CDCl$_3$) δ 197.3, 151.1, 128.7, 54.8, 53.5, 45.1, 36.3, 31.0, 29.7, 26.3, 24.0, 23.3, 22.6, 20.9, 18.0, 10.3 ppm; MS (EI) m/z 249 (M+) Trans isomer: Yield 0.61 g, 2.2 mmol (67%), mp 235° C. IR (KBr) 2928, 2592, 1668, 1457, 1394 cm$^{-1}$; $^1$H-NMR 500 MHz (CDCl$_3$) δ 3.06 (d, 1H, J=11.2 Hz), 2.72–2.78 (dt, 1H), 2.15–2.55 (m, 10H), 1.51–1.99 (m, 9H), 1.01–1.10 (dq, 1H), 0.89 (t, 3H) ppm; $^{13}$C-NMR 200 MHz (CDCl$_3$) δ

197.0, 152.6, 129.8, 59.6, 53.6, 51.2, 36.1, 35.2, 34.9, 29.3, 29.4, 28.1, 23.2, 20.8, 15.8, 10.4 ppm; MS (EI) m/z 249 (M+).

Example 7

1-Propyl-trans-2,3,4,4a,5,7,8,9,10,10a-decahydrobenzo[g]quinolin-6-one (GMC6650) and 1-Propyl-cis-2,3,4,4a,5,7,8,9,10,10a-decahydrobenzo[g]quinolin-6-one (GMC6651)

A solution of 3-ethynyl-2-cyclohexen-1-one (GMC6573) (Example 5a) (1.80 g, 15.0 mmol) in 1,2-dichlorobenzene (50 mL) was added to a solution of 1-propylamine-4-pentene in 1,2-dichlorobenzene (50 mL). The solution was stirred for 30 min at rt then for 72 h at 190° C. After cooling the mixture was poored in 4N HCl (40.0 mL) and this was stirred at rt for 2 h. The acidic layer was separated and extracted with diethylether (2×50 mL). Then the aqueous layer was made alkaline (pH=8) with concentrated ammonia and was extracted with dichloromethane (5×50 mL). The combined organic layers were washed with brine (50 mL) and dried (MgSO$_4$). Evaporation gave a dark oil that was purified by column chromatography (silica, dichloromethane/methanol, gradient) and subsequently converted to the hydrochloride, which was isolated in 2% yield. Analysis data were as in Example 6.

This procedure was repeated by rather than working in 1,2-dichlorobenzene solution the reactants were reacted neat at 300° C. When working in this way the yield was considerably improved.

Example 8

Resolution of 1-Propyl-trans-2,3,4,4a,5,7,8,9,10,10a-decahydrobenzo[g]quinolin-6-one (GMC6650)

A 5 mg mL$^{-1}$ solution of racemic GMC6650 prepared as illustrated in Example 6, in hexane/isopropanol (4/1 (v/v)) was injected into a HPLC system using a Water 510 HPLC pump fitted with a 500 μL loop and a Chiralpack AD semi-preparative column (250×10 mm). Mobile phase was a mixture produced by an ISCO Model 2360 Gradient Programmer and consisted of 98% hexane (containing 0.1% (w/w) triethylamine) and 2% isopropanol/hexane (1/1 (w/w)). Flow of the mobile phase was 4.0 mL min$^{-1}$. The separate enantiomers were detected by a Water 486 Millipore Tunable Absorbance Detector (λ=254 nm, AUFS=2.0) and were recorded on paper using a Kipp & Zonen flatbed recorder (chart speed 5 mm min$^{-1}$, α=1.33; k$_1$'=2.16; k$_2$'=2.88). Fractions were collected by hand. After evaporation of the mobile phase the optical rotation of the two fractions was determined using a Perkin Elmer 241 Polarimeter. First eluting fraction: [α]$_d^{20}$=+185° (c=0.08, methanol). Second eluting fraction: [α]$_d^{20}$=−214° (c=0.07, methanol). Both enantiomers were analyzed for their purity using the same HPLC system but now fitted with a Chiral-pack AD analytical column (250×4.6 mm) and a 20 μL loop (e.e.=>99.9% for both enantiomers). Both enantiomers were converted to their corresponding maleate salts and were recrystallized from ethanol/diethylether. Melting points: (+)-GMC6650.Maleate mp: 186° C., (−)-GMC6650.Maleate mp: 192° C.

Scheme 4) Prodrug of Benzo[f]quinolines:

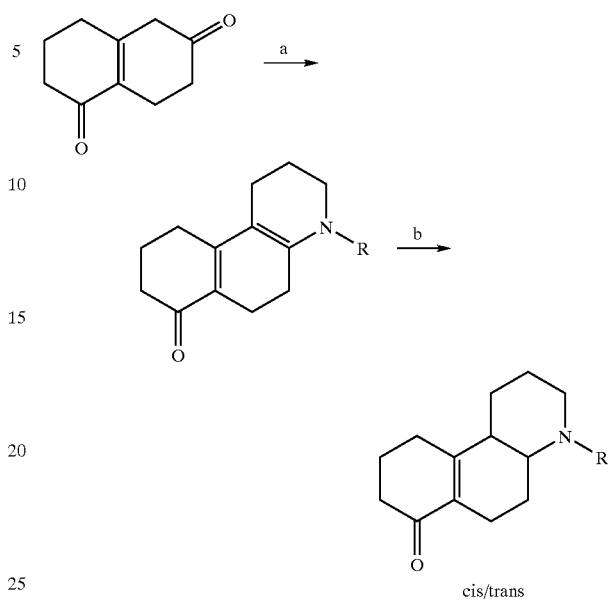

Reagents: (a) Chloropropyl-alkylamine; (b) NaBH$_3$CN

Example 9

N-Propyl-benzo[f]quinoline Prodrug

N-propyl-8,9-dihydro-10H-aporphin-11-one a) Method 1:

To a stirred solution of 3,4,7,8-tetrahydro-2H,5H-naphthalene-1,6-dione (0.5 g, 3.0 mmol) in dry acetonitril (15 mL) is added 3-chloropropyl-propylamine (0.38 g, 3,0 mmol). The mixture is heated to 80° C. under argon for 36 h. The reaction mixture is then cooled to RT and diluted with ether (25 mL). Filtration and evaporation of the solvents yields an oil that is dissolved in tetrahydrofuran (15 mL) and cooled to 0° C. The crude product is reduced with NaBH$_3$CN under acidic conditions. Work-up is performed in the usual way and the products are purified by column chromatography and the separated cis and trans products are subsequently converted to a pharmaceutically acceptable salt and recrystallized, yielding the desired products.

b) Method 2:

1,3-cyclohexadione (0.2 mol), paraformaldehyde (0.2 mol), (3-chloropropyl)-propylamine (0.2 mol) and powdered 4 Å molesieves are mixed in toluene. The mixture is heated and acetone (0.2 mol) is introduced and heating is continued. The reaction mixture is concentrated in vacuo then washed through a column of silica. The fractions containing the product are combined and concentrated. This material is further purified by column chromatography. The purified dienaminone is reduced with NaBH$_3$CN under acidic conditions. Work-up in the usual way and the products are purified by column chromatography and the separated cis and trans products are subsequently converted to a pharmaceutically acceptable salt and recrystallized, yielding the desired products.

Scheme 5) Syntheses of a Prodrug of Apomorphine:
Synthesis of the main building block:
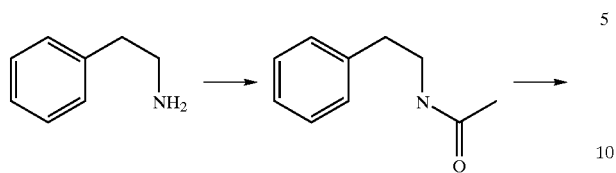
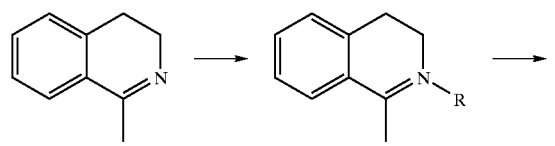
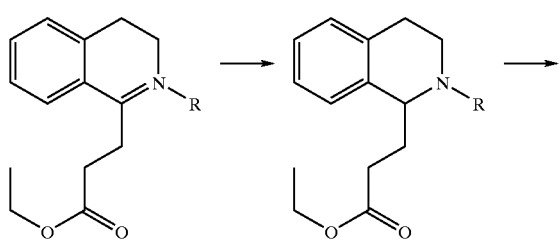
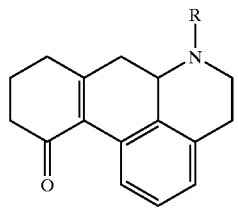
Reagents: (a) NaBH$_4$; (b) 6N HCl; (c) i) BrCH$_2$CONH$_2$, HCO$_2$H; ii) NaOH; (d) Wittig reaction; (e) PPA.
Benzyne strategy:
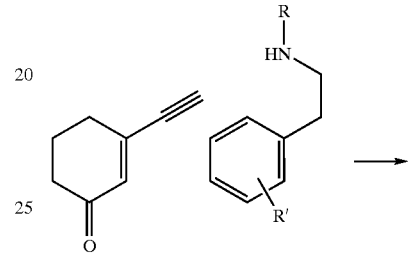
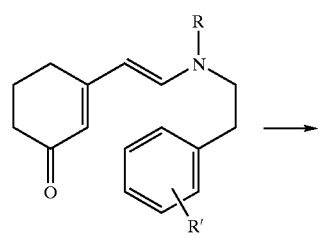
Keto-transposition and attachment of the 4$^{th}$ ring:
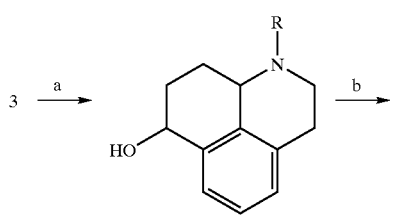
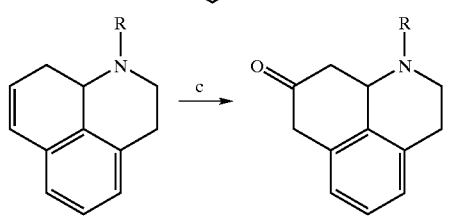
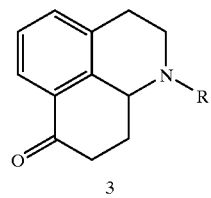
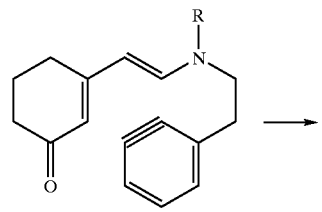
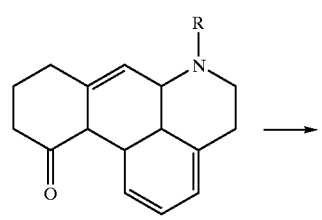
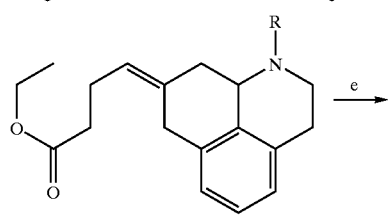
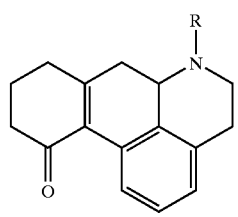
N-Propyl Aporphine Prodrug

Example 10 a) 3-aminophenylacetic acid ethyl ester (GMC6635)

To a cooled solution (−15° C.) of 3-aminophenylacetic acid (10.2, 67 mmol) in ethanol (200 mL) was added dropwise thionyl chloride (10 mL, 0.14 mol). The reaction mixture was stirred for 24 h allowing the temperature to slowly rise to rt. Evaporation of the volatiles gave a beige solid that was stripped several times with dichloromethane. The solid was then treated with hot diethyl ether and filtered to remove diethyl sulphite. Recrystallization from dietyl ether gave 14.4 g, 67 mmol, 100% of the desired compound as an off-white crystalline hydrochloride, mp 135° C. IR (KBr) cm$^{-1}$ 2857,2614, 1740 b) N-propyl-2-(3-aminophenyl)ethylamine (GMC6636)

3-Aminophenylacetic acid ethyl ester hydrochloride (2.7 g, 13 mmol) was added to n-propylamine (20 mL) while stirring and cooling to 0° C. After stirring for 45 min the reaction mixture was evaporated to give a colorless solid of the amide product. The amide was dissolved in tetrahydrofuran (20 mL) and 2N BH$_3$.SMe$_2$ in tetrahydrofuran (20 mL) was added at −10° C. After stirring at that temperature for 2 h the mixture was refluxed for 48 h. The mixture was extracted to give the amine which was converted to the hydrochloride salt. Recrystallisation from acetone/diethyl ether gave 2.2 g, 10 mmol (77%), mp 175° C. IR (KBr) 2928, 2592, 1457, 1394 cm$^{-1}$; MS (EI) m/z 178 (M$^+$).

c) N-propyl-8,9-dihydro-10H-11-oxo-aporphine (GMC6660)

A solution of 3-ethynyl-2-cyclohexen-1-one (GMC6573) (1.80 g, 15.0 mmol) in toluene (5 mL) was added to a solution of N-propyl-(3-aminophenylethyl)amine (2.67 g, 15.0 mmol, free base) toluene (5 mL). The solution was stirred for 30 min and subsequently extracted with 6N HCl solution (2×4 mL). The acidic solution was cooled to 0° C. and a solution of NaNO$_2$ (0.69 g, 100 mmol) in water (15 mL) was added slowly maintaining 0° C. After the addition was complete the mixture was allowed to warm up to RT and was stirred untill all starting material and diazonium intermediate were consumed. The acidic solution was extracted with ethyl acetate (2×20 mL), made alkaline (pH≈8), and was extracted with dichloromethane (4×20 mL). The combined organic layers were washed with saturated NaCO$_3$ solution (50 mL) and dried (MgSO$_4$). Evaporation gave an oil that was purified by column chromatography (silica, dichloromethane/ethanol, 40:1) and the pure product was subsequently converted to the hydrochloric salt to 3.18 g, 10 mmol (67%), mp 210–212° C. IR (KBr) 2948, 2851, 1661; $^1$H-NMR (CDCl$_3$) δ 5.86 (d, 1H), 2.48–2.67 (m, 6H), 2.27–2.39 (m, 6H), 1.96 (m, 2H), 1.02 (t, 6H) ppm; $^{13}$C-NMR (CDCl$_3$) δ 198.3, 163.5, 124.8, 48.9, 45.2, 35.7, 33.7, 28.4, 21.2, 10.1 ppm; MS (CI) m/z 282 (M+1).

Example 11

N-n-propyl-1,3,4,4a,5,6,8,9,10,10b-dekahydro-2H-benzo[f]quinolin-7-one

1-Propyl-7-oxo-2,3,7,8,9,9a-hexahydro-1H-benzo[de]quinoline is reduced to the corresponding alcohol and subsequently dehydrated. The exocyclic double bond is epoxidized followed by a ring opening thus forming 1-propyl-6-oxo-2,3,6,8,9,9a-hexahydro-1H-benzo[de]quinoline. This ketone is subjected to a Wittig reaction with (3-ethoxycarbonylpropyl)-triphenylphosphonium bromide. After the usual work-up the crude product is dissolved in dichloromethane and is added to PPA. After the cyclization is complete the product is allowed to hydrolyze under acidic conditions. Extraction after basification gives the crude end product. This is purified by column chromatography and the products were subsequently converted to a pharmaceutically acceptable salt and recrystallized.

Pharmacology

Behavioral Testing in Rats of Compound GMC6650 (Example 6)

One rat, weighing about 350 g, was injected SC in the neck with 1 μmol/kg of GMC6650. Another rat, weighing about 350 g, was injected PO with the same dose. The drug (3.4 mg) was initially dissolved in: ethanol (50 μL), 1 M acetic acid (2 drops), and water (1.4 mL), corresponding to 15 μmol per 1.5 mL, which means a concentration of 10 μmol/mL. By first diluting that solution 10 times and injecting 0.35 mL, the given dose will be 1 μmol/kgμmol/kg. This goes for both of rats.

Independent of which kind of administration the rats had received, both individuals displayed the same pattern of biological activity: after 10 minutes the rats became sedated, closing or partly closing their eyes. After 15 minutes obvious dopaminergic effects were seen, i.e. chewing, sniffing, licking, penile grooming, grooming, and after 30 minutes both rats showed clear signs of stereotypy.

Stereotypy was intense and was registered for several hours by visual inspection. After 10 hours both rats were still showing signs of stereotypy. The next morning, the SC rat was still active, while the PO rat was resting. Duration of action was thus ≧10 h for both sc and po administration of 1 μmol/kg.

The invention claimed is:

1. Compounds of the following general formula If:

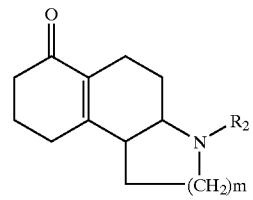

Formula If wherein m is an integer 1–3 and R$_2$ is selected from the group consisting of a hydrogen atom, alkyl or haloalkyl groups of 1 to 7 carbon atoms, cycloalkyl (alkyl) groups of 3 to 7 carbon atoms, alkenyl or alkylnyl groups of 3 to 6 carbon atoms, arylalkyl, heteroarylalkyl having 1 to 3 carbon atoms in the alkyl moiety, in which the aryl/heteroaryl may be substituted; and salts thereof with pharmaceutically acceptable acids or bases.

2. Compounds according to claim 1, wherein R$_2$ is n-propyl.

3. A method of treating Parkinson's disease in a patient in need thereof, which method comprises administering to the patient a therapeutically effective amount of a compound of formula If as defined in claim 1 or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 6,998,405 B2 | Page 1 of 1 |
| APPLICATION NO. | : 10/737782 | |
| DATED | : February 14, 2006 | |
| INVENTOR(S) | : Hakan Wikstrom et al. | |

It is certified that error appears in the above-identified patent and that said Letters Patent is hereby corrected as shown below:

Title Page, Item "(62) Related U.S. Application Data", change the text from "Division of application No. 10/258,014, filed as application No. PCT/SE01/00840 on Apr. 17, 2001, now Pat. No. 6,683,087" to -- Division of application No. 10/258,014, filed Oct. 18, 2002, now US Patent No. 6,683,087, which is a 371 of PCT/SE01/00840, filed Apr. 17, 2001. --.

Signed and Sealed this

Seventeenth Day of October, 2006

JON W. DUDAS
*Director of the United States Patent and Trademark Office*